(12) United States Patent
Fogelstrand

(10) Patent No.: US 11,668,918 B2
(45) Date of Patent: Jun. 6, 2023

(54) SYSTEM AND METHOD FOR FLUORESCENCE MICROSCOPY WITH DETECTION OF LIGHT EMISSION FROM MULTIPLE FLUOROCHROMES

(71) Applicant: Kromnigon AB, Gothenburg (SE)

(72) Inventor: Per Fogelstrand, Mölndal (SE)

(73) Assignee: KROMNIGON AB, Gothenburg (SE)

(*) Notice: Subject to any disclaimer, the term of this patent is extended or adjusted under 35 U.S.C. 154(b) by 0 days.

(21) Appl. No.: 15/627,601

(22) Filed: Jun. 20, 2017

(65) Prior Publication Data

US 2017/0285317 A1 Oct. 5, 2017

Related U.S. Application Data

(63) Continuation of application No. 15/100,646, filed as application No. PCT/SE2014/051484 on Dec. 11, 2014, now abandoned.

(30) Foreign Application Priority Data

Dec. 16, 2013 (SE) .................................. 1351503-6

(51) Int. Cl.
| | |
|---|---|
| *G02B 21/00* | (2006.01) |
| *G02B 21/16* | (2006.01) |
| *G01N 21/64* | (2006.01) |
| *G01N 33/58* | (2006.01) |
| *F21V 8/00* | (2006.01) |
| *G02B 21/06* | (2006.01) |

(Continued)

(52) U.S. Cl.
CPC ......... *G02B 21/16* (2013.01); *G01N 21/6458* (2013.01); *G01N 33/582* (2013.01); *G02B 6/0001* (2013.01); *G02B 21/06* (2013.01); *G02B 21/088* (2013.01); *G01N 2021/6419* (2013.01); *G01N 2021/6421* (2013.01); *G01N 2021/6441* (2013.01); *G01N 2021/6471* (2013.01); *G02B 26/008* (2013.01)

(58) Field of Classification Search
CPC ...... G02B 21/16; G02B 21/06; G02B 21/088; G02B 6/0001; G01N 33/582; G01N 21/6458

See application file for complete search history.

(56) References Cited

U.S. PATENT DOCUMENTS

| | | |
|---|---|---|
| 5,863,504 A | 1/1999 | Heffelfinger |
| 2005/0250155 A1 | 11/2005 | Lesko |

(Continued)

FOREIGN PATENT DOCUMENTS

| | | |
|---|---|---|
| CN | 1707245 A | 12/2005 |
| CN | 101836152 A | 9/2010 |

(Continued)

OTHER PUBLICATIONS

Osborn, Filters for FISH Imaging, Connection, p. 102-107 (Year: 2009).*

(Continued)

*Primary Examiner* — Hugh Maupin
(74) *Attorney, Agent, or Firm* — RMCK Law Group, PLC

(57) ABSTRACT

The present invention relates to fluorescence microscopy and specifically to improvements of method for and a corresponding fluorescence microscopy system for allowing separate detection of a plurality of fluorochromes.

20 Claims, 8 Drawing Sheets

(51) Int. Cl.
*G02B 21/08* (2006.01)
*G02B 26/00* (2006.01)

(56) References Cited

U.S. PATENT DOCUMENTS

| | | | |
|---|---|---|---|
| 2005/0270639 A1 | 12/2005 | Miki | |
| 2008/0032414 A1 | 2/2008 | Zhuang | |
| 2010/0032568 A1* | 2/2010 | Fraser | ............... G01N 21/6456 |
| | | | 250/336.2 |
| 2010/0294947 A1 | 11/2010 | Oda et al. | |
| 2011/0043907 A1 | 2/2011 | Sasaki | |
| 2011/0174986 A1 | 7/2011 | Kempe et al. | |
| 2012/0314206 A1 | 12/2012 | Spizig et al. | |
| 2014/0203191 A1 | 7/2014 | Buijsse et al. | |

FOREIGN PATENT DOCUMENTS

| | | | |
|---|---|---|---|
| CN | 101932925 A | 12/2010 | |
| CN | 101285932 | 3/2011 | |
| CN | 103513411 A | 1/2014 | |
| JP | 2008139796 A | 6/2008 | |
| JP | 2010284101 | 12/2010 | |
| JP | 4968575 B2 | 7/2012 | |
| WO | 0026666 | 5/2000 | |
| WO | 2009001390 | 12/2008 | |
| WO | 2013147317 | 10/2013 | |

OTHER PUBLICATIONS

Abcam, A guide to fluorochromes, 1 page (Year: 2012).*
Amersham Biosciences Fluorescence Imaging Handbook, pp. 136-139 (Year: 2002).*
European Search Report, EP Counterpart Application No. EP14872537; dated Aug. 14, 2017, European Patent Office, Munich, Germany.
Asako Sawano; Multicolor imaging of CA2+ and protein kinase C signals using novel epifluorescence microscopy; Feb. 1, 2002, pp. 1076-1085, vol. 82, No. 2, Biophysical Journal, Elsevier, Amsterdam, NL.
International Search Report, Parent International Application No. PCT/SE2014/051484; dated Apr. 14, 2015, International Search Authority/Sweden Patent Office, Stockholm, Sweden.
William Mason; Office Action for EPO Counterpart Application No. 14872537.7; European Patent Office, Munich DE, dated Sep. 10, 2018.
Extended European Search Report dated Nov. 4, 2020 for EP Application No. 20170591.0, 22 pages.
Chinese Search Report dated Jun. 20, 2022 for Chinese Patent Application No. 202010099834.8, 3 pages.

* cited by examiner

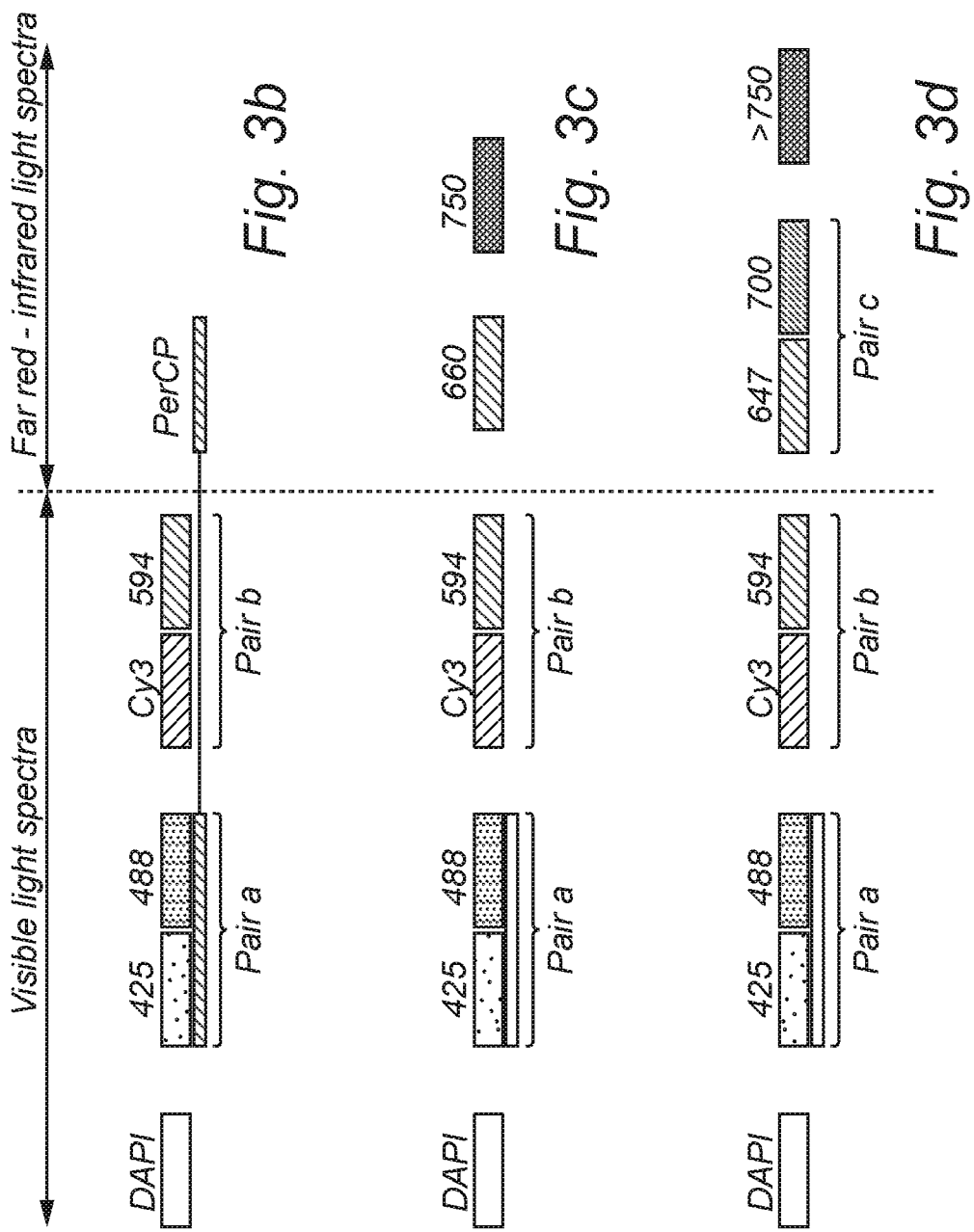

*Six-channel setup that can be used with a mercury lamp*
*(a and b index fluorochrome pairs)*

| Filter set | Excitation filter (wavelength / bandwidth) | Emission filter (wavelength / bandwidth) |
| --- | --- | --- |
| DAPI | 350/50 nm | 445/50 nm |
| 425[a] | 442/10 nm | 480/10 nm |
| 488[a] | 497/16nm | 525/15 nm |
| Cy3[b] | 546/10 nm | 568/10 nm |
| 594[b] | 591/6 nm | 620/14 nm |
| PerCP | 442/10 nm | 690/50 nm |

*Fig. 4a*

*Seven-channel setup that can be used with a xenon lamp or a metal halide lamp + LED support*
*(a and b index fluorochrome pairs)*

| Filter set | Excitation filter (wavelength / bandwidth) | Emission filter (wavelength / bandwidth) |
| --- | --- | --- |
| DAPI | 350/50 nm | 445/50 nm |
| 425[a] | 442/10 nm | 480/10 nm |
| 488[a] | 497/16nm | 525/15 nm |
| Cy3[b] | 546/10 nm | 568/10 nm |
| 594[b] | 591/6 nm | 620/14 nm |
| 660 | 655/15 nm | 690/8 nm |
| 750 | 740/13 nm | 780/12 nm |

*Fig. 4b*

*Nine-channel setup that can be used with a xenon lamp or a metal halide lamp + LED support*
*(a, b, c and d index fluorochrome pairs)*

| Filter set | Excitation filter (wavelength / bandwidth) | Emission filter (wavelength / bandwidth) |
| --- | --- | --- |
| DY-350XL[a] | 360/12 nm | 605/15 nm |
| BV421[a] (or DY-360XL[a]) | 387/11 (360/12 nm) | 420/10 (448/20 nm) |
| 425[b] | 442/10 nm | 480/10 nm |
| 488[b] | 497/16 nm | 525/15 nm |
| Cy3[c] | 546/10 nm | 568/10 nm |
| 594[c] | 591/6 nm | 620/14 nm |
| 647[d] | 640/14 nm | 670/10 nm |
| 700[d] | 690/8 nm | 720/13 nm |
| 790 | 760/12 nm | 800/12 nm |

Examples of fluorochromes with similar spectra (fluorochrome analogs)

| Category | Examples of fluorochromes |
|---|---|
| DAPI | DAPI, Hoechst, CF350, AF350, Dylight350, AMCA |
| BV421 | BV421, AF405, CF405S, Dylight405, HiLyteFluor405, |
| 425 | Atto425, DY-415, PromoFluor415, CFP, Sytox blue |
| 488 | FITC, GFP, eGFP, AF488/500, Atto488, CF488, PromoFluor505, Dylight488, HiLyteFluor488 |
| Cy3 | Cy3, AF488/555, Atto550, CF543/555, PromoFluor546/555, DY-555, Dylight549 |
| 594 | TexasRed, AF594, Atto590/594, AttoRho13, CF594, HiLyteFluor594 |
| 647 | AF647, Cy5, Atto647/647N, HiLyteFluor647, DY-656 |
| 660 | AF660, Atto655/665, CF660C/R, Cy5.5, DY-673, Draq5, RedDot |
| 680 | AF680, CF680, Dylight680, Atto680, DY-675/676/680, |
| 700 | Atto700, DY-700/701, IRDye700 |
| 750 | AF750, Dylight750, Atto750, CF750, HiLyteFluor750, Cy7 |
| 790 | CF790, AF790, Dylight800, IRDye800, |

Fig. 6

SYSTEM AND METHOD FOR FLUORESCENCE MICROSCOPY WITH DETECTION OF LIGHT EMISSION FROM MULTIPLE FLUOROCHROMES

TECHNICAL FIELD

The present invention generally relates to fluorescence microscopy, and more specifically to improvements of a method for a microscopy system and a corresponding fluorescence microscopy system for allowing separate detection of a light emission from a sample labeled with a plurality of different fluorochromes.

BACKGROUND OF THE INVENTION

Fluorescence microscopy is a light microscopy technique for studying the structure or properties of a sample by imaging fluorescent or phosphorescent emission from target species, such as organic molecules or inorganic compounds, located on or in the sample. For instance, the sample may be labeled with one or a plurality of different fluorochromes (also denoted as fluorophores), molecules that when they absorb light they subsequently dispose of their increased energy by various means, one of which is the emission of light of longer wavelengths.

When such a molecule is irradiated with ultraviolet, visible, far red, near infrared or infrared light, it may undergo an electronic transition during which the molecule absorbs a quantum of energy, and an electron is excited from the orbital it occupies in the ground state to another orbital of higher energy. The wavelength spectra at which the irradiated molecules absorb light is called absorption spectra or excitation spectra. Most excited states are short-lived and the major fate of the absorbed energy is reemission of light as phosphorescence or fluorescence. The wavelength spectra at which the irradiated molecules emit light is called emission spectra. The fluorescent properties of organic and inorganic dyes provide the basis for a number of analytic methods, one of which is immunofluorescence, which uses fluorochrome-conjugated antibodies to detect proteins and other molecules.

An exemplary fluorescence microscope typically used for such analysis comprises a light source, optics to convey light into an excitation light pathway, an excitation filter to select one or more excitation wavelength bands to be conveyed to the object, a dichroic mirror configured to reflect the excitation wavelength bands to the sample while transmitting the fluorescent emission wavelengths from the sample to the emission optical pathway, an emission filter to block any stray excitation light wavelengths transmitted into the emission optical pathway and optics to convey the fluorescence emission wavelengths to the eye or to an image capturing device such as a camera.

Generally, all modern microscopes are provided with a multiplicity of rapidly switchable "filter cubes", each filter cube being dedicated to a specific fluorochrome (or a set of similar fluorochromes) and include a matched set of excitation filter, dichroic mirror, and emission filter. The separate and sequential visualization of different fluorochromes can easily be accomplished by switching through the matching filter sets one-at-a-time in succession.

Such sequential visualization of different fluorochromes each having a separate excitation/emission wavelength spectra, can for example be used to reveal the spatial location of two (or more) proteins within a tissue, by the use of fluorescence proteins (e.g GFP) or fluorochrome-labeled antibodies (so-called immunofluorescence), or detection of two (or more) DNA mutations in cells, by the use of fluorochrome-labeled nucleic acids (probes).

In such studies, there is often a desire to combine many channels to gain information. For example, in biological studies it is common to visualize several different cell types within a tissue sample, by using cell-specific antibodies labeled with different fluorochromes. However, today only a limited number of fluorophores are allowed to be strongly separated within the same sample, because of light emission bleedthrough from different fluorochromes. The problem with bleedthrough (also referred to as spill-over artifacts) may be solved by compensation, i.e. computer-based calculations that compensate for addition of signals from partly overlapping fluorochrome spectra. However, this is a complicated process not routinely used in research or laboratory medicine.

Accordingly, there would be desirable to provide for a method and microscopy system configured for simplified separation of and improved detection of light emission from more than four different fluorochromes.

SUMMARY OF THE INVENTION

According to a first aspect of the invention, the above is at least partly alleviated by a method for detecting fluorescence emitted from a sample labeled with a plurality of predetermined fluorochromes using a microscopy system comprising a light source arrangement, wherein the method comprises the steps of selecting at least four different fluorochromes configured to emit light within the visible light spectra, the at least four different fluorochromes including a first and a second fluorochrome forming a pair of fluorochromes, selecting excitation wavelength intervals for the at least four different fluorochromes, wherein the excitation wavelength interval for the second fluorochrome is selected such that the excitation of the first fluorochrome is reduced, configuring a filter arrangement of the microscopy system to selectively allow light to pass through within emission wavelength intervals matching the emission wavelength intervals of the at least four different fluorochromes, wherein the emission wavelength interval for the first fluorochrome is selected to reduce light emission bleedthrough from the second fluorochrome, sequentially emitting light within, at least a portion of the selected excitation wavelength intervals, and detecting light emitted from the sample transmitted through the filter arrangement, wherein the pair of fluorochromes are selected as a Cy3 analog fluorochrome forming the first fluorochrome and a 594 analog fluorochrome forming the second fluorochrome, or the pair of fluorochromes are selected as a 425 analog fluorochrome forming the first fluorochrome and a 488 analog fluorochrome forming the second fluorochrome. A fluorochrome pair can also be formed by using two fluorochromes with different stoke shifts. Stoke shifts is the shift between the excitation wave length interval and the emission wave length interval. In this way the two fluorochromes can be activated by the same excitation light interval, and be separated by two different emission filters configured so that the emission wavelength interval for the first fluorochrome is selected to reduce light emission bleedthrough from the second fluorochrome, and the emission wavelength interval for the second fluorochrome is selected to reduce light emission bleedthrough from the first fluorochrome. This may for example be beneficial when using light-emitting diodes (LEDs, further discussed below) instead of excitation filters to activate fluorochromes, since one LED can be used to activate two fluorochromes. In a preferred embodiment, a fluorochrome with a large stoke shift can be added on top of a fluorochrome pair, thus forming a fluorochrome triplet. This can for example be achieved with PerCP combined with the 425/488 pair.

The invention is based on the understanding that by solving the primary problem of separating fluorescence signals emitted from a sample labeled with a first fluorochrome and a second fluorochrome, advantages will follow with reduced complications for also allowing the separation of further fluorescence signals basing from a third and a fourth (different) fluorochrome, constrained to the case where the fluorochromes emits light within the visible spectra (e.g. typically within the range of 400-640 nm) and the first and the second fluorochromes are either a combination/pair of fluorochromes being a Cy3 analog fluorochrome and a 594 analog fluorochrome, respectively, or the first and the second fluorochromes are a combination/pair of fluorochromes being a 425 analog fluorochrome and a 488 analog fluorochrome, respectively. This is according to the invention achieved by selecting an excitation wavelength interval for the second fluorochrome such that the excitation of the first fluorochrome is reduced and by selecting an emission wavelength interval for the first fluorochrome such that light emission bleedthrough from the second fluorochrome is reduced.

Within the scope of the invention it is possible to allow signal separation of the at least four fluorochromes. However, every sample does not need not necessarily at any given time be labeled with the at least four fluorochromes. Accordingly, at least four fluorochromes that may be separated are made available by means of the invention but not necessarily all sequentially excited "at the same time", e.g. in some embodiments only one, two or three of the at least four fluorochromes may be excited, but the microscope has the capacity to separate signals from any of the at least four fluorochromes.

In regards to one of the above discussed pairs of fluorochromes, the term "Cy3 analog fluorochrome" and "594 analog fluorochrome" should be interpreted in its broadest sense (see FIG. 6 for examples on fluorochromes with similar excitation and emission spectra), including any organic or inorganic compound that has a similar excitation/emission spectrum. It should be noted that the list are non-exclusive and further present and future equivalent fluorochromes may be contemplated and within the scope of the invention.

In regards to another one of the above discussed pairs of fluorochromes, the term "425 analog fluorochrome" and "488 analog fluorochrome" should be interpreted in its broadest sense (see FIG. 6 for examples on fluorochromes with similar excitation and emission spectra), including any organic or inorganic compound that has a similar excitation/emission spectrum.

In addition, based on molecular complexity and synthetic methods, the general term "fluorochrome" should be interpreted broadly, including any type of fluorochrome based on proteins and peptides, small organic compounds, synthetic oligomers and polymers, or multi-component systems, expressions that are well known in the art. Based on the application, the type of fluorochrome used may differ. That is, in non-live samples it is generally desirable to select a photostable fluorochrome, whereas in relation to for example a "live imaging" application (including live sample) it is typically necessary to select a fluorochrome having characteristics such as for example being non-toxic. Any application may be possible in relation to the inventive method.

The separation of the fluorescence signals from the at least four fluorochromes will have great advantages in the area of fluorescence microscopy, specifically since it will allow "screening" of a large panel of proteins in a few tissue samples. Furthermore, it enables advanced co-localization analyses, where several proteins can be visualized within the same sample (e.g. for multicolor analysis). In addition, it greatly simplifies the use of fluorescence microscopy for users, as they can choose to label samples with any of the fluorochromes that the filter sets can separate without thinking about potential bleedthrough artifacts. The separation of the fluorescence signals may also have great advances in other fluorescence reader systems than microscopes, for example spectrophotometers used for western blot, PCR and ELISA.

The method preferably also comprises the step of labeling the sample with the at least four different fluorochromes. There are at present available pluralities of different methods of labeling a sample, the labeling methods being dependent on the type of sample as well as what part of the sample it is desirable to label. Accordingly and as understood by the skilled addressee, samples can for example be labeled with fluorochrome-labeled antibodies, cell membrane dyes, DNA-binding fluorochromes, fluorochrome-labeled nucleic acid probes, and fluorescent proteins for collecting information about the biology and pathology of proteins, DNA, cells and tissues from humans, animals, plants, and microorganisms.

In a preferred embodiment of the invention, five different fluorochromes are selected and the method is adapted accordingly. Hence, in such an embodiment, one pair of fluorochromes are selected as the Cy3 analog fluorochrome forming the first fluorochrome and the 594 analog fluorochrome forming the second fluorochrome, and a further pair of fluorochromes are selected as the 425 analog fluorochrome forming the first fluorochrome and the 488 analog fluorochrome forming the second fluorochrome.

It may additionally be possible to also include at least one further additional fluorochrome, emitting light within the far red spectra (e.g. typically within the range of 640-680 nm), allowing for the separation of one further fluorescence signal. Still further, it may also be possible to include at least one further fluorochrome, emitting light within the near infrared spectra (e.g. typically above 680 nm). These additional fluorochromes may include individually as well or instead of separating both the above two discussed pairs of "visible" spectrum fluorochromes.

In a preferred embodiment, the remaining fluorochromes are further selected from a group comprising a DAPI analog fluorochrome or a BV421 analog fluorochrome, a 425 analog fluorochrome, a 488 analog fluorochrome, Cy3 analog fluorochrome, a 594 analog fluorochrome, a 647/660/680 analog fluorochrome or a PerCP analog fluorochrome, and a 750/790 analog fluorochrome.

Selecting further fluorochromes with emission in the far red/near infrared spectra may make it possible to separate as many as five, six or even seven fluorescence signals from each other (i.e. without including further computer based processing as discussed above), still using an illuminating light source of ultraviolet and visible light, such as a mercury lamp or metal halide lamp (possibly with the addition of a light source for excitation within the infrared spectra). Examples of far red/near infrared and infrared analog fluorochromes for 647/660/680/700/750 and 790 are shown in FIG. 6.

Using a light source that emit light with high energy also above 620 nm, such as a xenon lamp or LEDs, enables the formation of a pair of fluorochromes that emit light in the far red/near infrared spectra, selected as a 647 analog fluorochrome forming the first fluorochrome and a 700 analog fluorochrome forming the second fluorochrome. As discussed above for visible fluorochrome pairs, the excitation wavelength interval for the second fluorochrome is selected such that the excitation of the first fluorochrome is reduced, and the emission wavelength intervals the first fluorochrome is selected to reduce light emission bleedthrough from the second fluorochrome. Advantages will follow with reduced complications for also allowing the separation of further fluorescence signals basing from a third and fluorochrome, constrained to the case where the fluorochromes emits light at the upper infrared spectra, typically above 750 nm.

In a preferred embodiment, using illumination source(s) that emit light with high energy at the ultraviolet, visible, far red, near infrared and infrared spectra, the remaining fluorochromes are further selected from a group comprising a DAPI analog fluorochrome or a BV421 analog fluorochrome, a 425 analog fluorochrome, a 488 analog fluorochrome, Cy3 analog fluorochrome, a 594 analog fluorochrome, a 647 analog fluorochrome, a 700 analog fluorochrome, and a 790 analog fluorochrome. On top of this it is possible to add fluorochrome with huge stoke shifts.

According to another aspect of the invention there is provided a microscopy system for separating fluorescence signals emitted from a sample labeled with a plurality of predetermined fluorochromes, the microscopy system comprising a light source arrangement configured to emit light, a light guide for guiding light from the light source arrangement to the sample for excitation of the plurality of predetermined fluorochromes, a filter arrangement configured to allow separation of fluorescence emitted by the plurality of predetermined fluorochromes labeling the sample, and a detection device configured for receiving light transmitted through the filter arrangement, wherein the microscope filter sets can separate signals from at least four different fluorochromes that emit light within the visible light spectra including a first and a second fluorochrome forming a pair of fluorochromes, the light source arrangement is configured to sequentially emit light within at least four different excitation wavelength intervals, the excitation wavelength interval for the second fluorochrome is selected to reduce excitation of the first fluorochrome, the filter arrangement comprises at least four matched filters configured to allow light to pass through within at least four different emission wavelength intervals, the emission wavelength interval for the first fluorochrome is selected to reduce light emission bleedthrough from the second fluorochrome, and the pair of fluorochromes are selected as a Cy3 analog fluorochrome forming the first fluorochrome and a 594 analog fluorochrome forming the second fluorochrome, or the pair of fluorochromes are selected as a 425 analog fluorochrome forming the first fluorochrome and a 488 analog fluorochrome forming the second fluorochrome.

In a preferred embodiment of the invention the detection device comprises an image capturing device configured to catch images of fluorescence of the sample. Such an image capturing device may be a camera connected to a computer. In sequentially capturing and storing a plurality of images relating to light emitted by each of the fluorochromes, it may be possible to "overlay" the images "on-top" of each other for example for providing multicolor analysis of the sample. It should be noted that the microscopy system/camera/connected computer may be configured for "live imaging" where a continued (sequential) stream of images (e.g. video stream) is captured of the sample, i.e. by "over time" acquiring more than one image for each of the fluorochromes.

Preferably, the light source arrangement comprises a source of ultraviolet and visible light and at least four matched filters configured to allow light to pass through within the at least four different excitation wavelength intervals. The light source may for example be a mercury lamp, a metal halide lamp, or a xenon arc lamp. Other suitable light sources are of course possible and within the scope of the invention. In a typical application, the at least four matched filters configured to allow light to pass through within the at least four different excitation wavelength intervals ("excitation filters") and the filter arrangement comprises at least four matched filters configured to allow light to pass through within at least four different emission wavelength intervals ("emission intervals") are arranged in four separate "filter cubes", respectively, further comprising a dichroic mirror. If a fluorochrome with large stoke shift is used, the excitation interval (or emission filter interval) can be shared by two different fluorochromes. Accordingly, in such an implementation the filter arrangement may be seen as comprising four different filter cubes specifically adapted for allowing separation of the at least four fluorochromes in the manner as discussed above. Furthermore, in such an implementation, the inventive concept may be applicable as a "retro-fit" application where the inventive concept is selected for adapting an available microscopy system where a new "set" of filter cubes are provided allowing for the execution of the inventive concept.

However, in an alternative embodiment the light source arrangement may comprise a plurality of light-emitting diodes (LEDs). In such an embodiment it may not necessarily be of need to include specific excitation filters since the LEDs may be selected to be narrow banded and configured to inherently emit light within each of the specifically selected excitation wavelength. If LEDs are used, it may be beneficial to form fluorochrome pairs based in different stoke shifts, where both fluorochromes in the pair are activated by one LED. This would reduce the number of LEDs that are needed to activate a panel of fluorochromes.

Further features of, and advantages with, the present invention will become apparent when studying the appended claims and the following description. The skilled addressee realize that different features of the present invention may be combined to create embodiments other than those described in the following, without departing from the scope of the present invention.

BRIEF DESCRIPTION OF THE DRAWINGS

The various aspects of the invention, including its particular features and advantages, will be readily understood from the following detailed description and the accompanying drawings, in which:

FIG. 4a-c show different examples of specific filter setups;

FIG. 5 is a flow chart illustrating the method steps for detecting fluorescence from a sample labeled according to the invention, and FIG. 6 is a table showing examples of fluorochromes with similar excitation and emission spectra (fluorochrome analogs).

DETAILED DESCRIPTION

Figure 1:
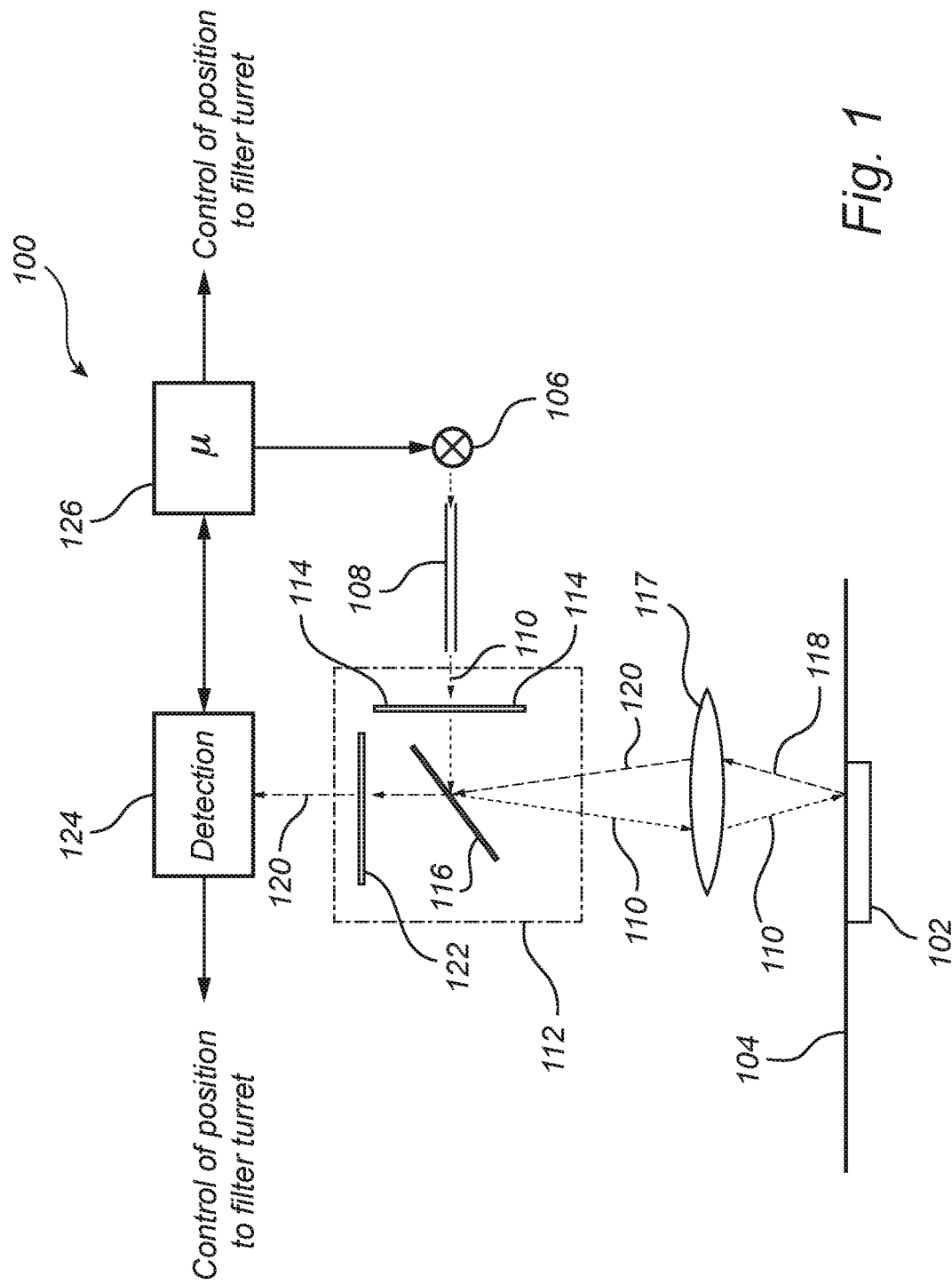
FIG. 1 shows an exemplary microscopy system according to the invention.

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

Referring now to the drawings and to FIG. 1 in particular, there is depicted a microscopy system 100 according to a preferred embodiment of the invention. The microscopy system 100 is in operation used for imaging a sample 102 arranged on a microscope stage 104. The sample 102 is labeled with a plurality of different fluorochromes that absorb light at an excitation wavelength and, in response to that light, fluoresce, emitting light at emission wavelengths longer than the excitation wavelengths.

A light source 106 emitting light within the ultraviolet and visible spectrum (i.e. typically strong emission within the range between 350-620 nm), such as a mercury lamp or a metal halide lamp, generates light at the excitation wavelength of the fluorochromes and the light source 106 is coupled to a fiber 108, which carries an excitation beam 110 from light source 106 to a filter cube 112. In some embodiments, light emitted from light source 106 passes directly to filter cube 112 without being carried by a fiber. In other embodiments, excitation beam 110 passes through optical elements, such as lenses and apertures, before arriving at a filter cube 112. Excitation beam 110 enters the filter cube 112 that is arranged in a turret (not shown) of the microscopy system 100. The turret is provided for allowing a plurality of different filter cubes to be sequentially positioned within the optical axis between the light source 106 and the sample 102.

The filter cube 112 comprises a band pass excitation filter 114 which receives excitation beam 110 from fiber 108 and only transmits a part of the excitation beam 110 having a wavelength interval within the excitation wavelength interval of one of the fluorochromes used to label the sample 102. Excitation beam 110 is transmitted through excitation filter 114 and is received by a dichroic mirror 116, which reflects light at the excitation wavelength of the fluorochromes and transmits light at the emission wavelength of the fluorochromes. Excitation beam 110 is thus reflected by dichroic mirror 114. Dichroic mirror 114 is typically oriented diagonally within filter 112, typically at a 45 degrees angle relative to the direction of the excitation beam 110, such that the excitation beam 110 is reflected toward the sample 102.

Furthermore, the excitation beam 110 passes through an objective lens 117 and impinges on sample 102, where it excites the fluorochromes being present in sample 102. The fluorochromes fluoresce, emitting fluorescence light 118 at the emission wavelength of the fluorochromes. The fluorescence 118 is collected by the objective lens 117 and formed into an emission beam 120 which enters the filter cube 112. The emission beam 120 is then transmitted through dichroic mirror 116 and strikes an emission filter 122 also comprised with the filter cube 112. The emission filter 122 is also a band pass filter (or in some cases a long pass filter) that transmits light around the emission wavelength of the fluorochromes and reflects other light, such as, for example, stray light from the excitation beam and emission light from other fluorochromes in the sample 102. Emission beam 120 is thus transmitted through emission filter 122 and is directed out of microscopy system 100 to a thereto connected detection device 124. The detection device 124 may for example be a sensor, a spectrophotometer, a CCD or CMOS camera, or an eyepiece. In some embodiments, optical elements, such as lenses or beam splitters, are present between emission filter 122 and detection device 124 in order to appropriately direct emission beam 120. In case of the detection device 124 comprising a digital camera, such as a for example a CCD or CMOS camera, an automatic shutter is typically included for exposure control of the collected images (a video stream may also be captured as discussed above). It is common to use a monochrome camera to individually capture the emission from each fluorochrome, apply a false color digitally, and overlay them to get a final image when using a plurality of different filter cubes 112.

The microscopy system 100 further (typically) comprises a control unit 126 for controlling the operation of the microscopy system 100, including the position of the turret, the detection unit 124 and the light source 106. The control unit 126 may include a general purpose processor, an application specific processor, a circuit containing processing components, a group of distributed processing components, a group of distributed computers configured for processing, etc. The processor may be or include any number of hardware components for conducting data or signal processing or for executing computer code stored in memory. The memory may be one or more devices for storing data and/or computer code for completing or facilitating the various methods described in the present description. The memory may include volatile memory or non-volatile memory. The memory may include database components, object code components, script components, or any other type of information structure for supporting the various activities of the present description. According to an exemplary embodiment, any distributed or local memory device may be utilized with the systems and methods of this description. According to an exemplary embodiment the memory is communicably connected to the processor (e.g., via a circuit or any other wired, wireless, or network connection) and includes computer code for executing one or more processes described herein.

As mentioned above, the turret allows for removable insertion and positional control of a plurality of filter cubes 112. That is, as each type of fluorochrome has its own unique excitation and emission spectra, a different combination of excitation filter 114, dichroic mirror 116, and emission filter 122 are used for each type of fluorochrome. Thus, a filter cube having a specific combination of filters and mirror is assembled for use with a particular type of fluorochrome. Depending on the type of fluorochromes present in sample 102, a filter cube 112 having an appropriate combination of filters and mirror is accordingly inserted into the turret. Similarly, the filters and mirror in the filter cube 112 are selected for use with a particular light source.

The standard optical configurations described above use microscope optics to directly produce an enlarged image of the specimen on the camera sensor in order to capture a high resolution image of the specimen. This optical system is commonly referred to as' wide field 'microscopy. Those skilled in the art of microscopy will recognize that a high resolution image of the specimen can be created by a variety of other optical systems.

Figure 2A:
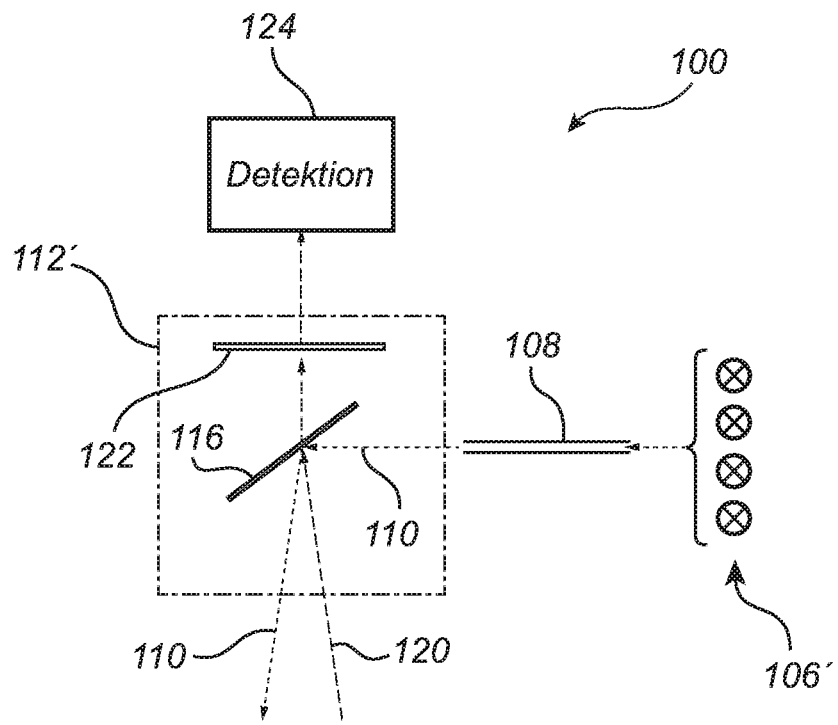
FIGS. 2a-2c illustrate alternative filter set-ups for the microscopy system.
Figure 2B:
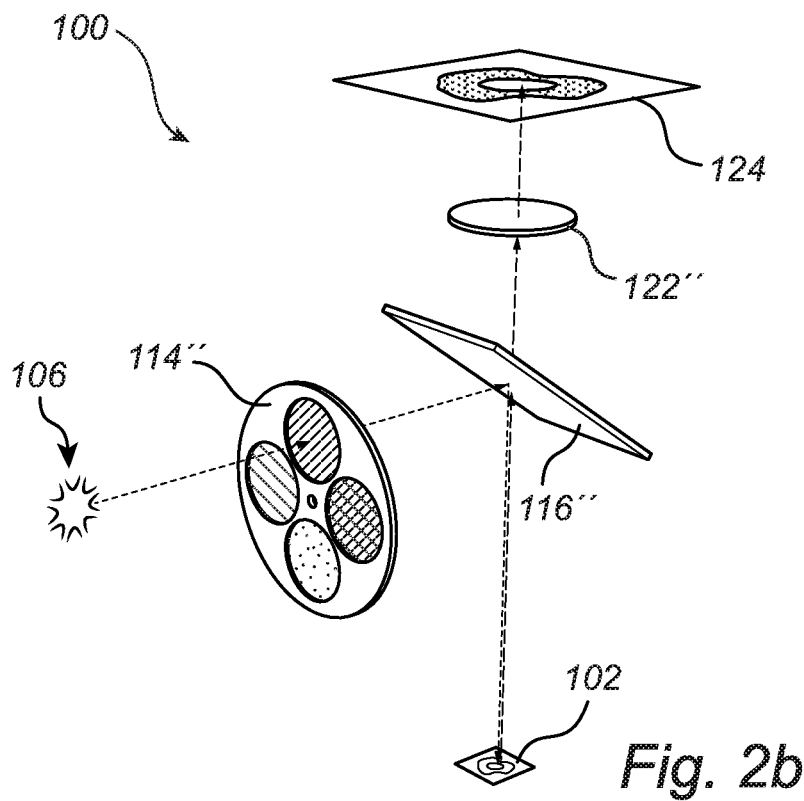
Figure 2C:
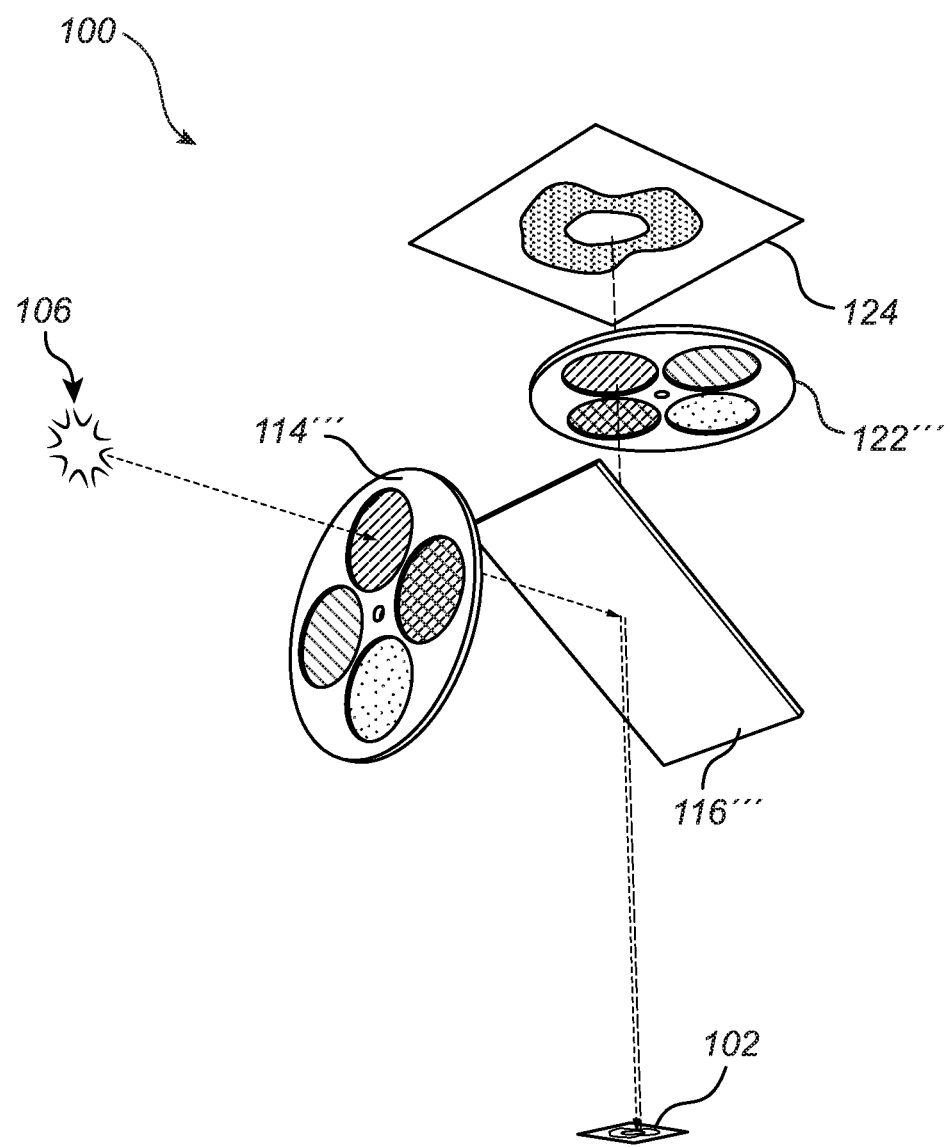

Turning briefly to FIGS. 2a-2c illustrating alternative implementation of the filter and light source arrangements for performing the concept according to the invention. In FIG. 2a the inventive concept is exemplified in a similar manner as in FIG. 1, however, instead of providing a single light source such as a mercury lamp (or similar) a plurality of LEDs 106' are provided, wherein each of the LEDs 106' are narrow banded LEDs typically emitting light only within a limited wavelength range, for example having a bandwidth around 20-50 nm. Accordingly, in using such an arrangement it may be possible to exclude the excitation filter of the filter cube 112'. Accordingly, each of the LEDs 106' must be tuned to only transmits components of the excitation beam 110 having a wavelength interval within the excitation wavelength interval of a one of the fluorochromes used to label the sample 102 (as discussed above).

Alternatively, the inventive concept may be implemented according to a so called "Pinkel" (FIG. 2b) or a "Sedat" (FIG. 2c) configuration. Both the Pinkel and the Sedat configuration incorporate a multiband dichroic; however differ in the combination of excitation and emission filters used. The Sedat filter configuration uses both single-band exciters and single-band emitters, while the Pinkel configuration uses single-band excitation filters and a multiband emitter. The S/N ratio achieved while using a Pinkel set is potentially higher than when using a full multiband configuration, although when comparing multiband filter sets, the Sedat configuration will, in most cases, give the highest signal-to-noise ratio. In comparison to the filter cube implementation shown in FIG. 1, the Pinkel and/or the Sedat configuration may possibly allow for very fast switching of introducing different filter configurations.

In addition, all of the different implementations illustrated in FIGS. 1 and 2a-2c are shown as implementing a "light reflecting strategy", i.e. light is impinged onto the sample 102 and then reflected back towards the detection device 124. It should however be understood that the inventive concept may be implemented also by allowing light to be transmitted "through" the sample 102, e.g. thus allowing the detection device 124 to be arranged "behind" the sample 102, or at any other angels.

Figure 3A:
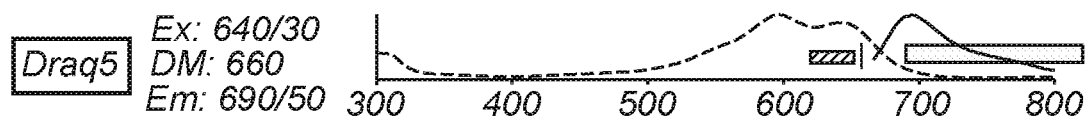
FIG. 3a shows an excitation/emission diagram for a plurality of different fluorochromes applied in accordance to the invention, and 3b-3d schematically illustrate some variants of fluorochrome analog setups in accordance to the invention.
Figure 3A:
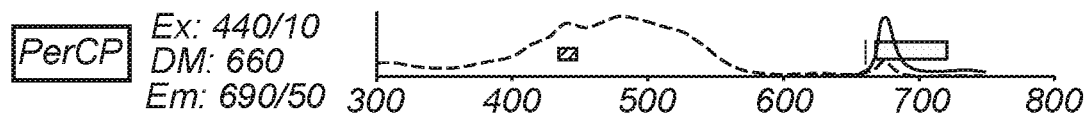
Figure 3A:
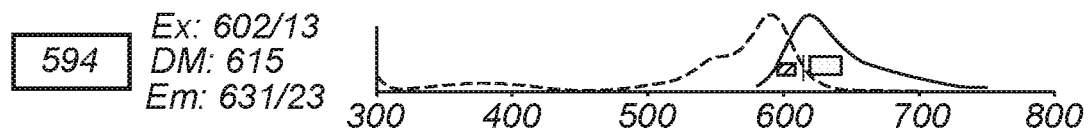
Figure 3A:
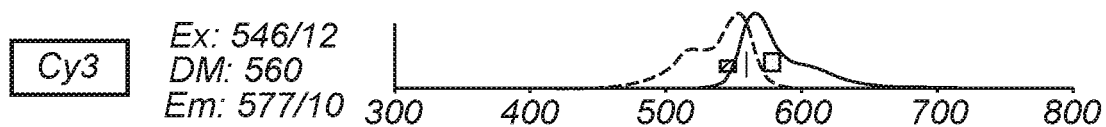
Figure 3A:
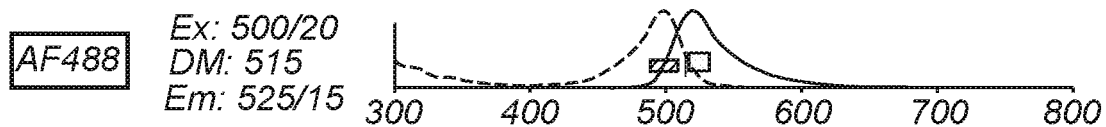
Figure 3A:
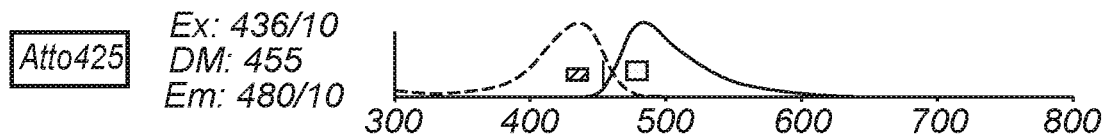
Figure 3A:
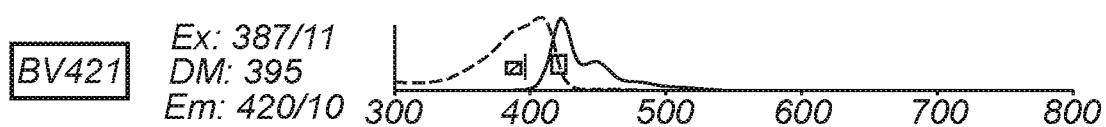

Turning now to FIG. 3a which shows an excitation/emission diagram for a plurality of different fluorochromes applied in accordance to the invention. In the illustration of FIG. 3a, the sample 102 has been labeled with seven different fluorochromes, thus forming seven different fluorescence signals being provided to the detection device 124.

As discussed above, the general problem solved by the invention is the separation of the signals from a sample labeled with the first fluorochrome and at the same time labeled with the second fluorochrome forming a pair of fluorochromes. As discussed above, the first and the second florochromes are selected from fluorochromes emitting light within the visible spectra (e.g. typically within the range of 400-640 nm), and the first and the second fluorochromes are either a combination/pair of fluorochromes being a Cy3 analog fluorochrome and a 594 analog fluorochrome, respectively, or the first and the second fluorochromes are a combination/pair of fluorochromes being a 425 analog fluorochrome and a 488 analog fluorochrome, respectively.

Typically, these fluorochromes are bright and have spectral overlap (425 in comparison to 488, and Cy3 in comparison to 594. In an exemplifying embodiment of the invention the 594 excitation filter has been shifted above 590 nm (e.g. 594/8 or 602/13 nm) which accordingly makes it possible to excite 594 without exciting Cy3. Furthermore, by shifting the emission filter of Cy3 below 580 nm (e.g. 568/10 or 572/10 nm), it has surprisingly been possible to collect the Cy3 emission signal without collecting the 594 emission signal. With these optimizations, the Cy3 filter arrangements (light and filter components) and the 594 filter arrangement makes it possible to separate the signals from each fluorochrome. Importantly, the fluorescence signals remained sufficiently strong with the optimized filter sets. A similar adaptation may in another example be made for the combination of a 425 and a 488 analog fluorochrome, and for the combination of a 647 and a 700 analog fluorochrome.

Next, the signal-to-noise ratio of the 488/FITC (fluorescein isothiocyanate) channel has been optimized by reducing autofluorescence from the tissue, which is a common issue for 488/FITC detection. Many molecules within tissues get activated by light in the blue spectra, for example mitochondrial proteins, collagen and elastin, which give rise to autofluorescence and emit light over a wide wavelength interval. By shifting the excitation filter above 490 nm (500/20 nm) the major part of autofluorescence vanished and significantly improved the signal-to-noise ratio. Care must be taken to choose a 488/FITC emission filter (525/15 nm) that does not collect any Cy3 emission signal. The shift of the 488/FITC emission filter gave room for an additional channel in-between DAPI and FITC (excitation above 420 nm and emission below 495). This interval is problematic regarding high tissue autofluorescence, and the fluorochrome needs to be bright enough to give an acceptable signal-to-noise ratio. There are only a handful fluorochromes available at this interval, and most of them are dim and/or affected to photobleaching. Nevertheless, Atto425 was found to be photostable and bright enough to override tissue autofluorescence. Also, the nuclei stain SytoxBlue fulfilled the criteria at this interval.

Finally, near infrared fluorochromes were selected/introduced/used to label the sample 102. Since a mercury lamp or a metal halide lamp is weak at wavelengths above 620 nm there are difficulties in getting enough light energy to properly excite near infrared fluorochromes. After testing a number of dyes, PerCP and its analogs (e.g. PerCP-Cy5.5) turned out to be superior. PerCP has a large (in comparison) Stoke shift and thus can be activated with high energy blue light, and its signal could easily be separated from the other fluorochromes in the setup, by forming a fluorochrome triplet with 425 and 488 analog fluorochromes. Among all infrared dyes tested with smaller (in comparison) Stoke shifts, it has been found that 647 analog fluorochromes, and some 660 analog fluorochromes (such as CF660R) gave reasonable good signal even when activated at a wavelength interval >620 nm. Thus, PerCP analog fluorochromes or 647 analog fluorochromes, and some 660 analog fluorochromes could be used in the multicolor setup and activated by a mercury lamp or a metal halide lamp.

Accordingly, by means of the invention it is possible to separately detect signals from four or more different fluorochromes that emit light within the visible spectrum. By also selecting fluorochromes that emit light within the far red spectrum (typically emitting light between 640 and 700 nm), near infrared spectrum (typically emitting light between 700 and 750 nm) or infrared spectrum (typically emitting light above 750 nm) it is possible to separate as many as seven different fluorescence signals. Further, i.e. more than seven different fluorescence signals could be possible to separate in case of using a light source (e.g. a "normal" light source for example in combination with further LEDs) emitting light within both the visible spectrum and above the visible spectrum (far red/near infrared/ infrared) in combination with fluorochromes being active in the far red/near infrared/infrared spectrum. The same concept is of course possible also for the ultra violet spectrum as well as for other light source combinations.

FIGS. 3b-3d illustrate alternative set-ups as how fluorochrome pairs can be combined with other fluorochrome pairs and other single fluorochromes in order to achieve multicolor setups in accordance to the invention. For example, FIG. 3b shows a multicolor setup that can be activated by a mercury lamp. Similarly, FIGS. 3c and 3d show multicolor setups that can be activated by a light source arrangement that also emit strong light in the far red/near infrared/ infrared spectra.

Below is given a possible combination of exemplifying fluorochromes (or any analog type) with suitable intervals to place excitation and emission filters within. The setup can be run with a mercury lamp or a metal halide lamp.

| Fluorochrome | Excitation filter (nm) | Emission filter (nm) |
| --- | --- | --- |
| DAPI | 330-380 | 420-500 |
| Atto425 | 415-450 | 455-485 |
| 488 | 480-520 | 500-535 |
| Cy3 | 535-555 | 555-590 |
| 594 | 585-615 | 605-655 |
| 647/660/680 or | 630-700 | 650- |
| PerCP | 420-500 | 645- |

Alternatively, in another embodiment of the invention the below combination may be possible. In this example the DAPI channel has been replaced with a fluorochrome pair that is activated by ultraviolet light (DY-350XL combined with DY-360XL or BV421), and a far red/near infrared fluorochrome pair is added (647 combined with 700). The setup preferably needs an illumination source that emits light with high energy at the far red and near infrared spectra to properly activate the 700 and 790 fluorochromes.

| Fluorochrome | Excitation filter (nm) | Emission filter (nm) |
| --- | --- | --- |
| DY-350XL | 320-390 | 540-680 |
| DY-360XL or BV421 | 320-390 or 380-415 | 420-460 or 410-440 |
| Atto425 | 425-450 | 455-480 |
| 488 | 480-515 | 500-535 |
| Cy3 | 535-555 | 555-595 |
| 594 | 590-615 | 600-655 |
| 647 | 630-665 | 645-685 |
| 700 | 685-715 | 695-750 |
| 790 | 744-800 | 695- |

Figures 4C, 5:
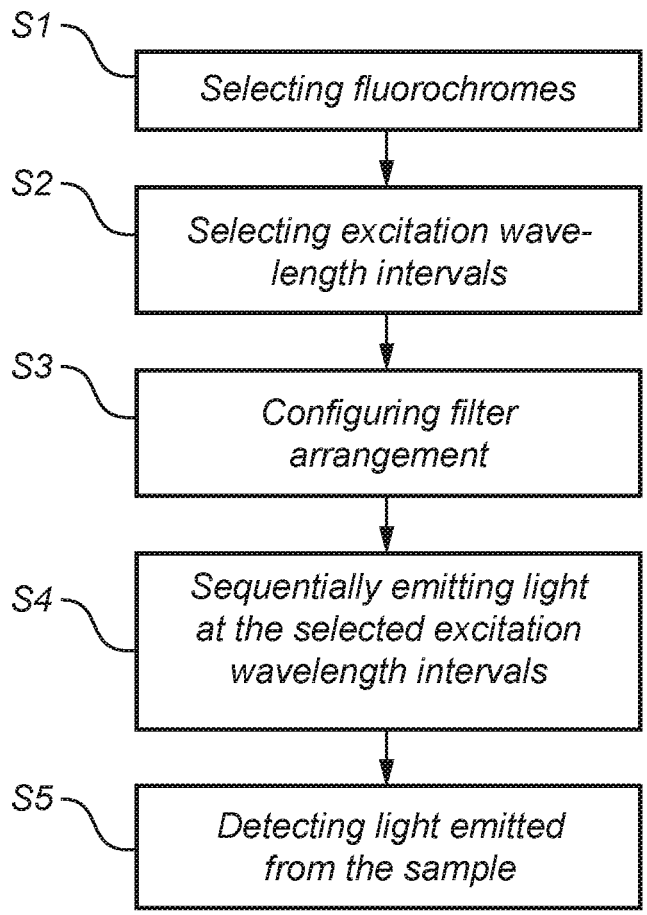

FIG. 4a-c show three specific examples of excitation and emission filter setups and their corresponding wavelength/ bandwidths.

Turning finally to FIG. 5 illustrating an exemplifying flow chart illustrating the method steps for operating the microscopy system 100 according to the invention. The process starts by the selection, S1, of at least four different fluorochromes including a Cy3 analog fluorochrome and a 594 analog fluorochrome. The at least four different fluorochromes are then used for labeling the sample 102, a sample being of any of the above discussed types.

Based on the fluorochromes selected to label the sample 102, a corresponding number (typically as many as the number of selected fluorochromes) excitation wavelength intervals are selected, S2, where the excitation wavelength interval for the second fluorochrome is specifically selected according to the above discussion and such that the excitation of the first fluorochrome is reduced. Then, the filter arrangement, e.g. the emission filter(s) of the filter cube(s) 112 (or alternatively according to the Pinkel or Sedat configuration) is selected, S3, to allow light to pass through within different emission wavelength intervals matching the emission wavelength intervals of the at least four different fluorochromes. Also here the general criteria should be met where the emission wavelength interval for the first fluorochrome is selected to reduce light emission bleedthrough from the second fluorochrome, where a Cy3 analog fluorochrome forms the first fluorochrome and a 594 analog fluorochrome forms the second fluorochrome, or a 425 analog fluorochrome forms the first fluorochrome and a 488 analog fluorochrome forms the second fluorochrome Using for example the control unit 126 in combination with light source 106, the turret and filter cubes 112 the microscopy system 100 is used to sequentially emit light, S4, within the selected excitation wavelength intervals. Either based on a reflecting light configuration or by allowing light to pass through the sample 102, light fluorescing from the fluorochromes used to label the sample 102 is for example under the control of the control unit 126 in combination with the digital camera (detection device 124) detected once the light has passed through the filter arrangement (typically at least including the emission filter).

As discussed above, images may be individually captured, a false color may be digitally applied, and the images may then be overlaid on top of each other for allowing the formation of a multicolor image. It may, as also discussed above, be possible to perform a live collection of subsequently collected images.

In summary, the present invention relates to a method for detecting fluorescence emitted from a sample labeled with a plurality of predetermined fluorochromes using a microscopy system comprising a light source arrangement, wherein the method comprises the steps of selecting at least four different fluorochromes configured to emit light within the visible light spectra, the at least four different fluorochromes including a first and a second fluorochrome forming a pair of fluorochromes, selecting excitation wavelength intervals for the at least four different fluorochromes, wherein the excitation wavelength interval for the second fluorochrome is selected such that the excitation of the first fluorochrome is reduced, configuring a filter arrangement of the microscopy system to selectively allow light to pass through within emission wavelength intervals matching the emission wavelength intervals of the at least four different fluorochromes, wherein the emission wavelength interval for the first fluorochrome is selected to reduce light emission bleedthrough from the second fluorochrome, sequentially emitting light within, at least a portion of the selected excitation wavelength intervals, and detecting light emitted from the sample transmitted through the filter arrangement, wherein the pair of fluorochromes are selected as a Cy3 analog fluorochrome forming the first fluorochrome and a 594 analog fluorochrome forming the second fluorochrome, or the pair of fluorochromes are selected as a 425 analog fluorochrome forming the first fluorochrome and a 488 analog fluorochrome forming the second fluorochrome.

The present invention also relates to a method for detecting fluorescence emitted from a sample labeled with a plurality of predetermined fluorochromes using a microscopy system comprising a light source arrangement, wherein the method comprises the steps of selecting at least six different fluorochromes configured to emit light within the visible, far red, and near infrared light spectra. The at least six different fluorochromes including a first and a second fluorochrome emitting light within the visible spectra forming a pair of fluorochromes, and a first and a second fluorochrome emitting light within the far red/near infrared spectra forming a pair of fluorochromes, selecting excitation wavelength intervals for the at least six different fluorochromes, wherein the excitation wavelength interval for the second fluorochrome is selected such that the excitation of the first fluorochrome is reduced, configuring a filter arrangement of the microscopy system to selectively allow light to pass through within emission wavelength intervals matching the emission wavelength intervals of the at least six different fluorochromes, wherein the emission wavelength interval for the first fluorochrome is selected to reduce light emission bleedthrough from the second fluorochrome, sequentially emitting light within, at least a portion of the selected excitation wavelength intervals, and detecting light emitted from the sample transmitted through the filter arrangement, wherein "visible" pair of fluorochromes are selected as a Cy3 analog fluorochrome forming the first fluorochrome and a 594 analog fluorochrome forming the second fluorochrome, or the pair of fluorochromes are selected as a 425 analog fluorochrome forming the first fluorochrome and a 488 analog fluorochrome forming the second fluorochrome, and the "non-visible" pair of fluorochromes are selected as a 647 analog fluorochrome forming the first fluorochrome and a 700 analog fluorochrome forming the second fluorochrome, The invention is based on the understanding that by solving the primary problem of separating fluorescence signals emitted from a sample labeled with a first fluorochrome and a second fluorochrome, advantages will follow with reduced complications for also allowing the separation of further fluorescence signals basing from a third and a fourth (different) fluorochrome within the visible spectra, constrained to the case where the fluorochromes emits light within the visible spectra (e.g. typically within the range of 400-640 nm). Furthermore, if a fluorochrome pair is also added within the far red/near infrared spectra (typically within the range of 640-750 nm), advantages will follow with reduced complications for also allowing the separation of further fluorescence signals basing from fluorochromes within the infrared spectra (typically above 750 nm). The first and the second fluorochromes are either a combination/pair of fluorochromes being a Cy3 analog fluorochrome and a 594 analog fluorochrome, respectively, or the first and the second fluorochromes are a combination/pair of fluorochromes being a 425 analog fluorochrome and a 488 analog fluorochrome, respectively, or the first and the second fluorochromes are a combination/pair of fluorochromes being a 647 analog fluorochrome and a 700 analog fluorochrome, respectively. This is according to the invention achieved by selecting an excitation wavelength interval for the second fluorochrome such that the excitation of the first fluorochrome is reduced and by selecting an emission wavelength interval for the first fluorochrome such that light emission bleedthrough from the second fluorochrome is reduced.

Although the figures may show a specific order of method steps, the order of the steps may differ from what is depicted. Also two or more steps may be performed concurrently or with partial concurrence. Such variation will depend on designer choice. All such variations are within the scope of the disclosure. Additionally, even though the invention has been described with reference to specific exemplifying embodiments thereof, many different alterations, modifications and the like will become apparent for those skilled in the art. Variations to the disclosed embodiments can be understood and effected by the skilled addressee in practicing the claimed invention, from a study of the drawings, the disclosure, and the appended claims. Furthermore, in the claims, the word "comprising" does not exclude other elements or steps, and the indefinite article "a" or "an" does not exclude a plurality.

The invention claimed is:

1. A method for detecting fluorescence emitted from a sample labeled with a plurality of predetermined fluorochromes using a microscopy system comprising a light source arrangement and a filter arrangement, wherein the method comprises the steps of:

selecting at least four different fluorochromes configured to emit light within the visible light spectra, the at least four different fluorochromes including a Cy3 fluorochrome, a 594 fluorochrome, a 488 fluorochrome, and a 647 fluorochrome, wherein the Cy3 and the 594 fluorochrome have a partly overlapping excitation spectrum and a partly overlapping emission spectrum;

selecting excitation wavelength intervals for the at least four different fluorochromes, wherein the excitation wavelength interval for the 594 fluorochrome is selected such that the excitation of the Cy3 fluorochrome is reduced and wherein:

the excitation wavelength interval for the Cy3 fluorochrome is 535-555 nm, the excitation wavelength interval for the 594 fluorochrome is 585-615 nm, the excitation wavelength interval for the 488 fluorochrome is 480-520 nm, and the excitation wavelength interval for the 647 fluorochrome is 630-665 nm;

selecting emission wavelength intervals for the at least four different fluorochromes;

configuring the filter arrangement of the microscopy system to:

selectively allow light to pass through within the selected emission wavelength intervals matching the emission wavelength intervals of the at least four different fluorochromes using a set of emission filters comprised with the filter arrangement, and selectively allow light to pass through within the excitation wavelength intervals matching the excitation wavelength intervals of the at least four different fluorochromes using a set of excitation filters comprised with the filter arrangement, wherein the emission wavelength interval for the Cy3 fluorochrome is selected to reduce light emission bleedthrough from the 594 fluorochrome and wherein:

the emission wavelength interval for the Cy3 fluorochrome is 555-590 nm, the emission wavelength interval for the 594 fluorochrome is 605-655 nm, the emission wavelength interval for the 488 fluorochrome is 500-535 nm, and the emission wavelength interval for the 647 fluorochrome has a lower end of 650 nm;

sequentially emitting light within the selected excitation wavelength intervals; and detecting light emitted from the sample transmitted through the filter arrangement wherein:
the excitation and emission wavelength intervals are selected to allow signal separation of the at least four fluorochromes to allow multicolor analysis with reduced bleedthrough artifacts when a single sample is labeled with the at least four fluorochromes.

2. The method according to claim 1, further comprising the step of separating fluorescence signals from the at least four different fluorochromes.

3. The method according to claim 1, further comprising selecting at least one further fluorochrome configured to emit light within the range of 640-680 nm or to emit light above 680 nm.

4. The method according to claim 1, further comprising selecting at least one further fluorochrome configured to emit light within the infrared spectra.

5. The method according to claim 1, further comprising selecting at least one further fluorochrome configured to emit light within the far red/near-infrared spectra.

6. The method according to claim 1, further comprising selecting at least one further fluorochrome comprising a DAPI fluorochrome, a BV421 fluorochrome, a 425 fluorochrome, a PerCP fluorochrome, a 660/680/700 fluorochrome, or a 750/790 fluorochrome.

7. The method according to claim 1, wherein the emission wavelength interval for the Cy3 fluorochrome is 555-580 nm.

8. The method according to claim 7, wherein the excitation wavelength interval for the 594 fluorochrome is 590-615 nm.

9. The method according to claim 1, wherein the excitation wavelength interval for the 594 fluorochrome is 590-615 nm.

10. A method for detecting fluorescence emitted from a sample labeled with a plurality of predetermined fluorochromes using a microscopy system comprising a light source arrangement and a filter arrangement, wherein the method comprises the steps of:
selecting at least four different fluorochromes configured to emit light within the visible light spectra, wherein the at least four different fluorochromes include a pair of fluorochromes comprising a first fluorochrome and a second fluorochrome;
selecting excitation wavelength intervals for the at least four different fluorochromes, wherein the first fluorochrome and the second fluorochrome share a same excitation wavelength interval;
configuring the filter arrangement of the microscopy system to selectively allow light to pass through within emission wavelength intervals matching the emission wavelength intervals of the at least four different fluorochromes, wherein the emission wavelength interval for the first fluorochrome is selected to reduce light emission bleedthrough from the second fluorochrome;
sequentially emitting light within the selected excitation wavelength intervals; and
detecting light emitted from the sample transmitted through the filter arrangement,
wherein the excitation and emission wavelength intervals are selected to allow signal separation of the at least four fluorochromes to allow multicolor analysis with reduced bleedthrough artifacts when a single sample is labeled with the at least four fluorochromes.

11. The method according to claim 10, wherein the light source arrangement comprises a plurality of light emitting diodes ("LEDs").

12. The method according to claim 11, wherein a single LED emits the same excitation wavelength interval of the first fluorochrome and the second fluorochrome.

13. The method according to claim 10, wherein the at least four different fluorochromes comprise a Cy3 fluorochrome and a 594 fluorochrome.

14. The method according to claim 13, wherein:
the excitation wavelength interval for the Cy3 fluorochrome is 535-555 nm;
the excitation wavelength interval for the 594 fluorochrome is 585-615 nm;
the emission wavelength interval for the Cy3 fluorochrome is 555-590 nm; and
the emission wavelength interval for the 594 fluorochrome is 605-655 nm.

15. The method according to claim 13, wherein the Cy3 and 594 fluorochrome have a partly overlapping excitation spectrum and a partly overlapping emission spectrum.

16. The method according to claim 13, wherein the emission wavelength interval for the Cy3 fluorochrome is selected to reduce light emission bleedthrough from the 594 fluorochrome.

17. The method according to claim 10, wherein the at least four different fluorochromes comprise a 488 fluorochrome and a 647 fluorochrome.

18. The method according to claim 17, wherein:
the excitation wavelength interval for the 488 fluorochrome is 480-520 nm;
the excitation wavelength interval for the 647 fluorochrome is 630-665 nm;
the emission wavelength interval for the 488 fluorochrome is 500-535 nm; and
the emission wavelength interval for the 647 fluorochrome has a lower end of 650 nm.

19. The method according to claim 10, further comprising selecting at least one further fluorochrome configured to emit light within the infrared spectra.

20. The method according to claim 10, further comprising selecting at least one further fluorochrome configured to emit light within the far red/near-infrared spectra.

* * * * *